United States Patent [19]

Beck et al.

[11] Patent Number: 5,130,661
[45] Date of Patent: Jul. 14, 1992

[54] TOMOGRAPHIC FLOW IMAGING SYSTEM

[75] Inventors: Maurice S. Beck, Altringham, United Kingdom; Andrzej B. Plaskowski, Warsaw, Poland; Song-Ming Huang, Beijing, China

[73] Assignee: The University of Manchester Institute of Science and Tech., Manchester, United Kingdom

[21] Appl. No.: 299,048

[22] Filed: Jan. 19, 1989

[30] Foreign Application Priority Data

Jan. 20, 1988 [GB] United Kingdom ............... 8801191

[51] Int. Cl.⁵ ............................................ G01R 27/26
[52] U.S. Cl. .................................. 324/663; 73/61.41; 324/672; 324/687; 324/688
[58] Field of Search ................... 324/61 R, 61 P, 658, 324/663, 664, 665, 603, 672, 686, 687, 688; 73/61 R, 61.1 R

[56] References Cited

U.S. PATENT DOCUMENTS 4,074,184  2/1978  Dechene et al. ............. 324/61 R X

OTHER PUBLICATIONS

Huang, Green, Stott and Beck, *A Proposed Capacitance Flow Imaging System*, Proceedings of the 3rd International Conference on Multiphase Flow, May 18-20, 1987.

Plakowski, Beck and Krawaczynski, *Flow Imaging for Multi-Component Flow Management*, Trans, Inst. MC, vol. 9, No. 9, Apr.-Jun. 1987, pp. 108-112.

Beck, Green, Allammer and Plaskowski, *Some Flow Imaging Problems*, IMC Conference on control and Instrumentation—The Changing Scene, Nov. 27-28, 1985, pp. 1-5.

Primary Examiner—Reinhard J. Eisenzopf
Assistant Examiner—Robert W. Mueller
Attorney, Agent, or Firm—Pravel, Gambrell, Hewitt, Kimball & Krieger

[57] ABSTRACT

A tomographic flow imaging system comprising three or more capacitance electrodes positioned around a pipe through which a flow to be monitored passes. The capacitance between each pair of the electrodes is measured, and an output is derived from the measured capacitances which is representative of the distribution of material within the pipe. A predetermined voltage signal is applied to one electrode at a time, and the electrodes other than said one electrode are connected to sources of equal fixed potential. The capacitance of each pair of electrodes is measured by measuring charge flowing between the said other electrode of the pair and the source of potential to which it is connected.

10 Claims, 8 Drawing Sheets

Electrode pair 1-2

SENSITIVITY PROFILE

Electrode pair 1-3

SENSITIVITY PROFILE

Electrode pair 1-4
SENSITIVITY PROFILE

Electrode pair 1-5
SENSITIVITY PROFILE

Electrode pair 1 – 2

Electrode pair 1 – 3

Electrode pair 1 – 4

Electrode pair 1 – 5

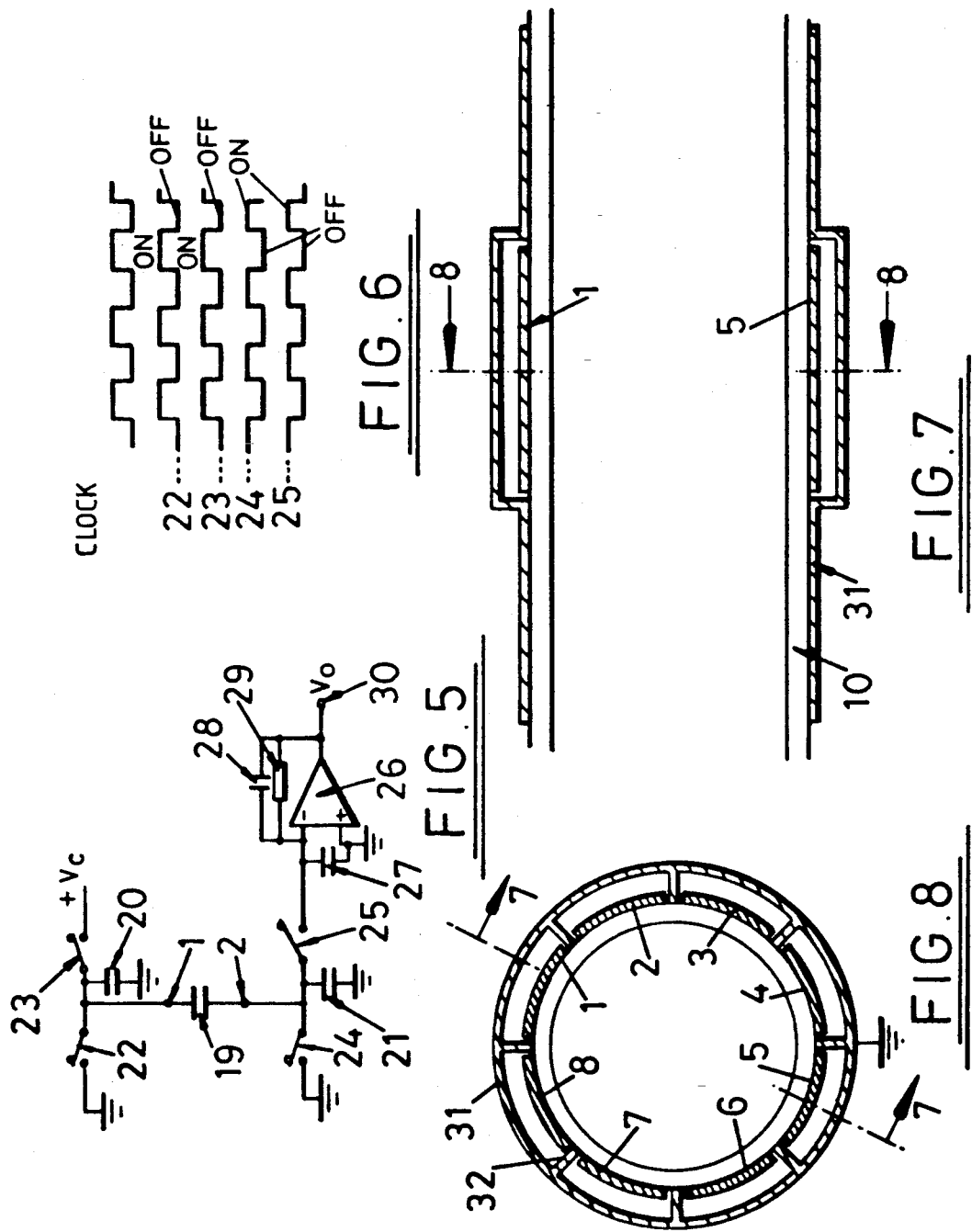

TOMOGRAPHIC FLOW IMAGING SYSTEM

The present invention relates to a tomographic flow imaging system for deriving an output representative of the distribution of material within a pipe through which a flow to be monitored passes.

As reported by Huang, S.M., Green, R.G., Stott, A. L., and Beck, M. S. in "Proceedings of the 3rd International Conference on Multiphase Flow", The Hague, Netherlands, 18-20 May 1987, it has been proposed to use capacitance sensing techniques to provide a simple and economic means for implementing flow imaging systems. The proposal envisaged the positioning of an array of electrodes, for example eight in total, around a pipe through which a multiphase flow passes. It was proposed to measure the capacitance between any two of the sensor electrodes and to reconstruct from this measured data an image of the component distribution within the pipe using an adaptation of back projection algorithms known from applied potential tomography developed for medical imaging purposes. It was suggested that stray-immune transducers would enable relatively small area of the pipe cross-section.

The implementation of the proposal outlined in the above report presented various problems. In particular in situations where the flow pattern can change rapidly, rapid data capture and processing is essential. Such situations are common in industrial processes. Furthermore, because of the differences between the distances separating various pairs of electrodes between which capacitance measurements must be made resulting from the distribution of the electrodes around the pipe, the measurements made with different electrode pairs have very different sensitivities. This considerably complicates the design of the measuring circuits required to measure the capacitance between the electrode pairs. Thus, although a practical electrode structure and a theoretical basis for obtaining useful data from that structure has been previously described, the details of an operational system have not.

It is an object of the present invention to provide a tomographic flow imaging system which enables the problems outlined above to be overcome.

According to the present invention, there is provided a tomographic flow imaging system, comprising three or more capacitance electrodes positioned around a pipe through which a flow to be monitored passes, means for measuring the capacitance between each pair of the electrodes, and means for deriving from the measured capacitances an output representative of the distribution of material within the pipe, wherein means are provided for applying a predetermined voltage signal to one electrode at a time, and means are provided for connecting the electrodes other than said one electrode to sources of equal fixed potential, the capacitance of each pair of electrodes being measured by measuring charge flowing between the said other electrode of the pair and the source of potential to which it is connected.

Preferably, the assembly of electrodes is housed within a conductive guard which extends around the pipe and is connected to one of said sources of equal fixed potential. The guard may comprise ribs which project radially inwards between adjacent electrodes.

Each of the electrodes may be connected to the predetermined voltage signal or alternatively to a respective charge measuring circuit the input of which is at the said equal fixed potential by a respective switching circuit. The switching circuits may be arranged such that all the measuring circuits operate simultaneously. Each charge measuring circuit may comprise an array of measuring circuits of different sensitivities, the switching circuit selecting a measuring circuit from the array which has a sensitivity appropriate to the electrode pair the capacitance between which is to be measured.

Preferably, the switching circuits are arranged such that for each pair of electrodes between which the capacitance is to be measured there are four switches, a first pair of the four switches being arranged to close simultaneously such that one electrode is connected to the said voltage signal and the other electrode is connected to a said source of fixed potential, and the other pair of the four switches being arranged to close after opening of the first pair such that the said one electrode is connected to a said source of fixed potential and the other electrode is connected to a charge measuring circuit.

Preferably, the means for deriving an output representative of the distribution of material within the pipe comprises means for constructing an image representative of the distribution. Preferably, the measured capacitance value is back-projected onto the positive sensing area of the field developed between the pair of electrodes between which the capacitance value is measured. The boundaries of the positive sensing areas may be calculated using finate element analysis methods. The cross-section of the pipe can then be considered as being made up of a series of positive elements (pixel) each made up from a different combination of parts of the various positive sensing areas. The grey level of each pixel is calculated by effectively summing the contributions of each positive sensing area within which it is included. The image pixels are then preferably filtered to eliminate artifacts produced by the back-projection.

The present invention also provides a circuit for measuring the capacitance of a capacitor formed by a pair of electrodes, comprising first and second pairs of switches arranged such that one switch of each pair is connected to a respective electrode, wherein a first switch of the first pair is connected between its respective electrode and a first source of fixed potential, a second switch of the first pair is connected between its respective electrode and a second source of fixed potential, a first switch of the second pair is connected between its respective electrode and the second source of fixed potential, and the second switch of the second pair is connected between its respective electrode and an input to a charge measuring circuit, the said input being maintained at the potential of the said second source of fixed potential, and means being provided to close the first pair of switches to charge the said capacitor, and to then open the first pair of switches and close the second pair of switches to discharge the capacitor into the charge measuring circuit.

An embodiment of the present invention will now be described, by way of example, with reference to the accompanying drawings, in which.

Figure 1:
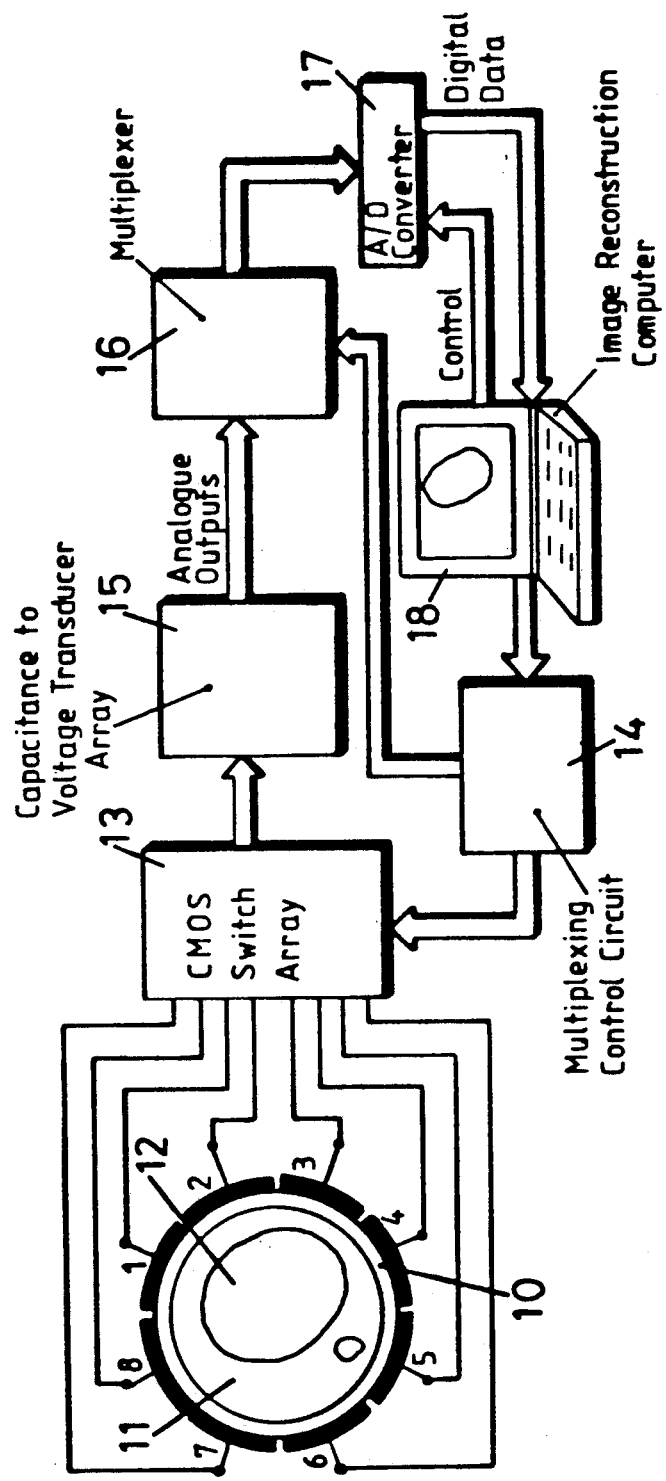
FIG. 1 is a block schematic illustration of a tomographic flow imaging system in accordance with the present invention.
Figure 2A:
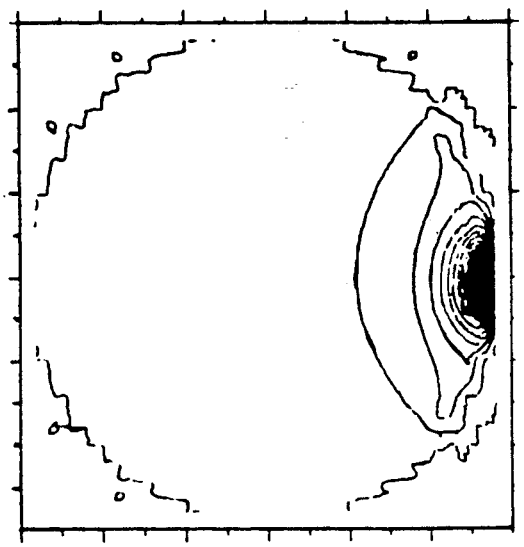
FIGS. 2A to 2D illustrate the measurement sensitivity distribution between four alternative electrode pairs in an eight electrode array of the type illustrated in FIG. 1, the sensitivity numbers shown on the figures having been multiplied by one thousand.
Figure 2B:
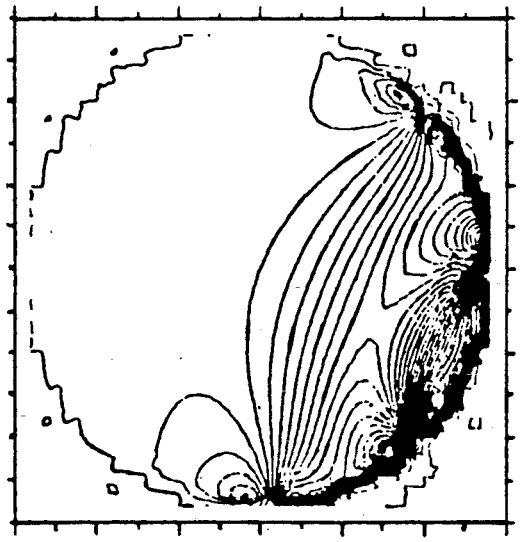
Figure 2C:
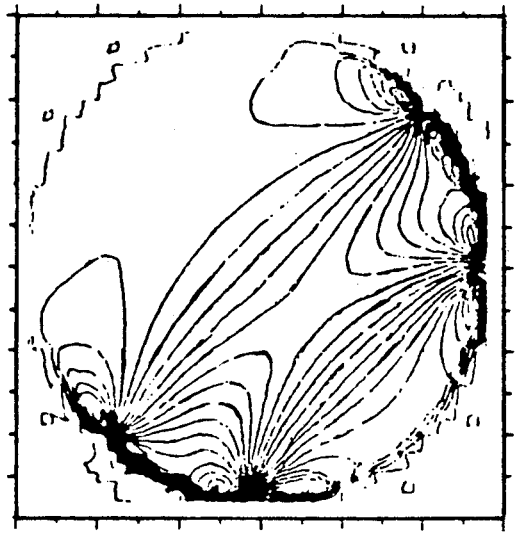
Figure 2D:
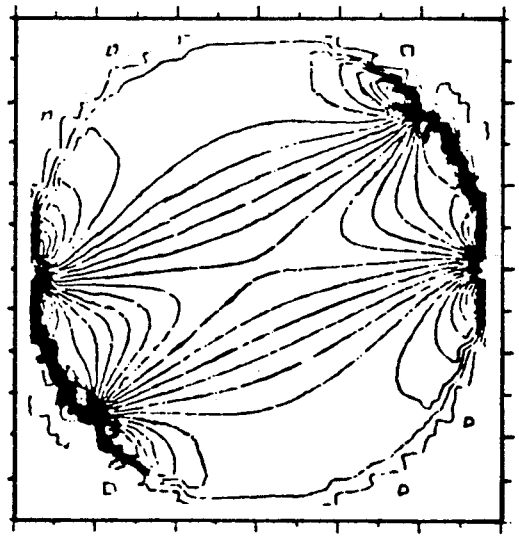
Figure 3:
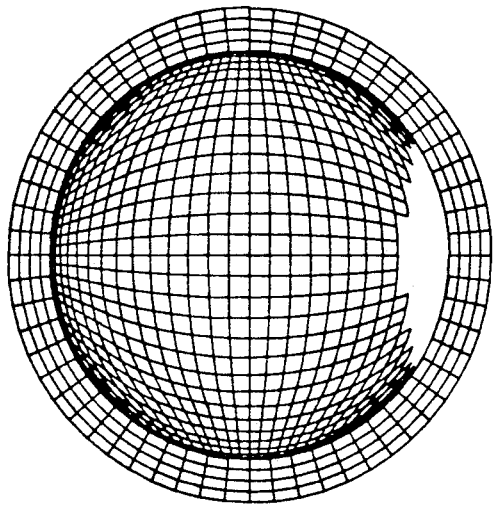
Figure 3:
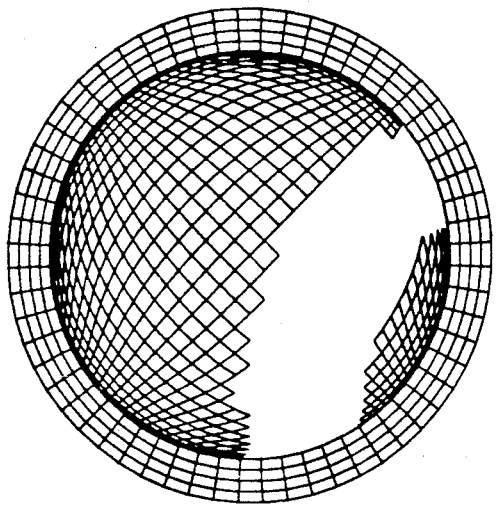
Figure 3:
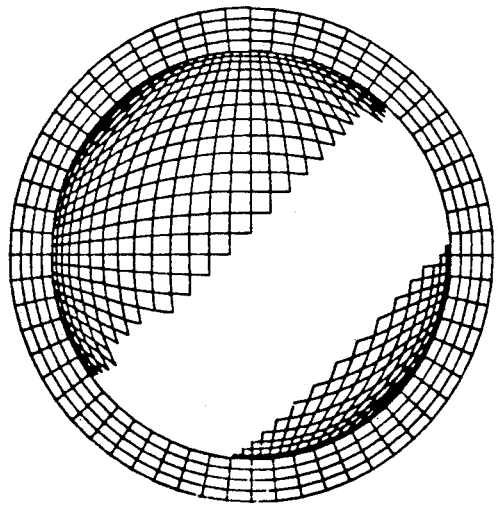
Figure 3:
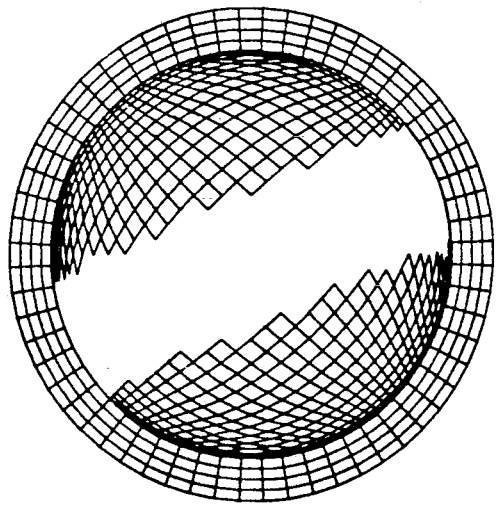
Figure 10:
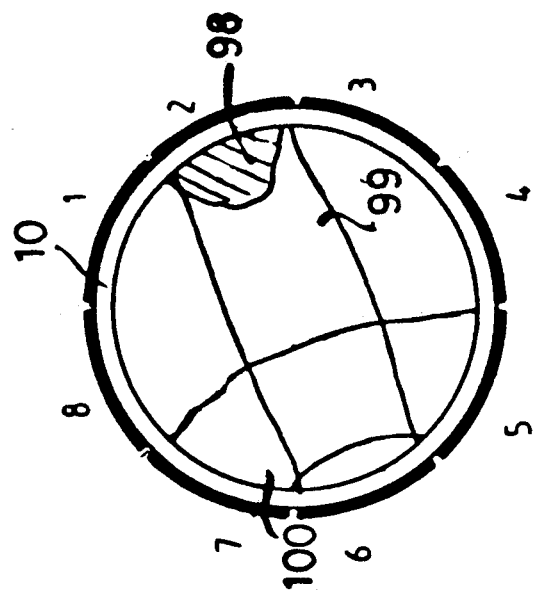
Figure 4:
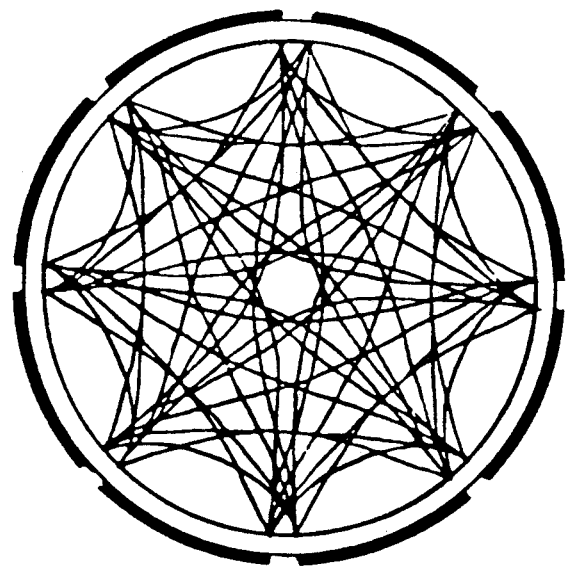
Figure 9:
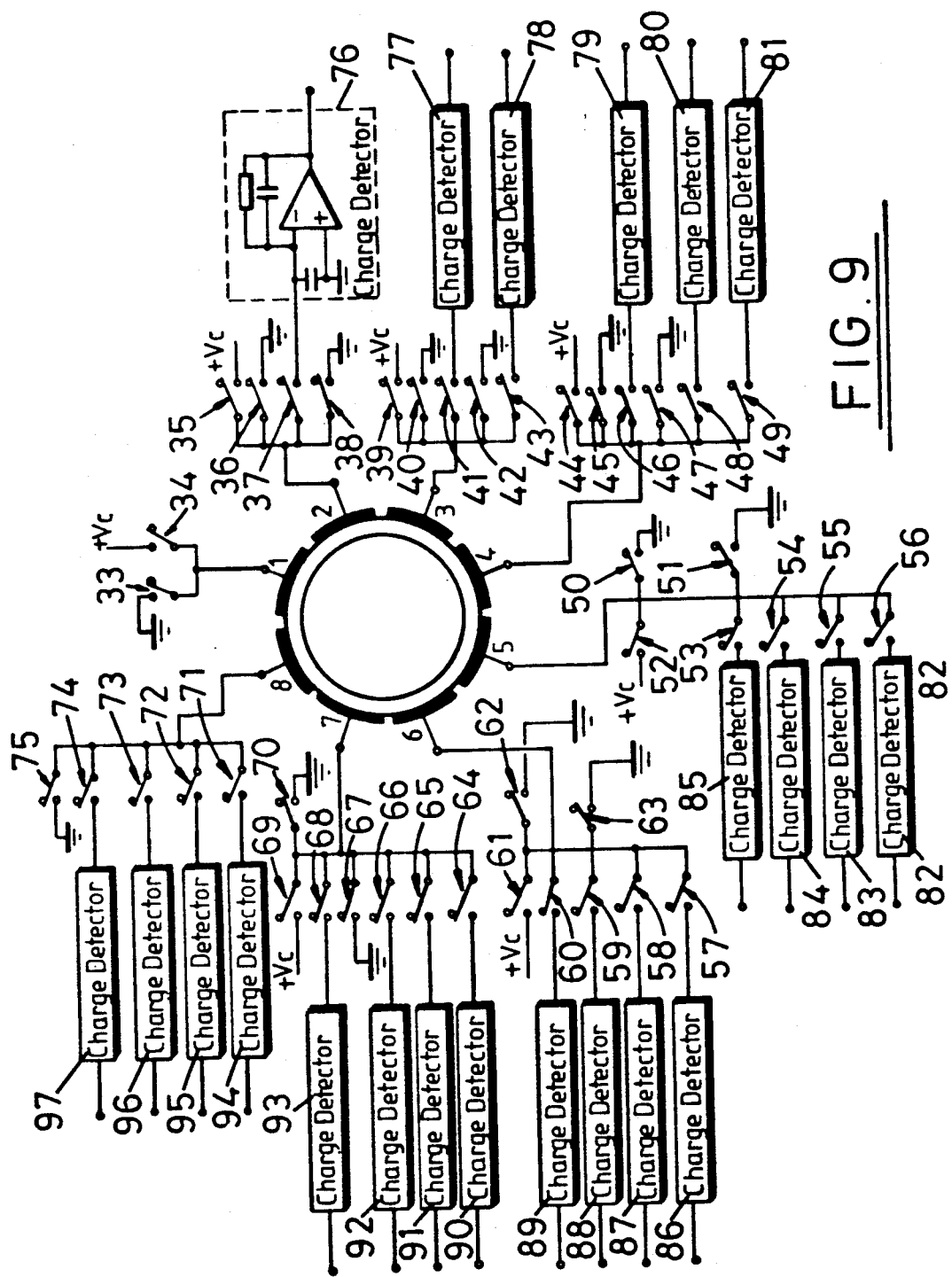
Figure 11A:
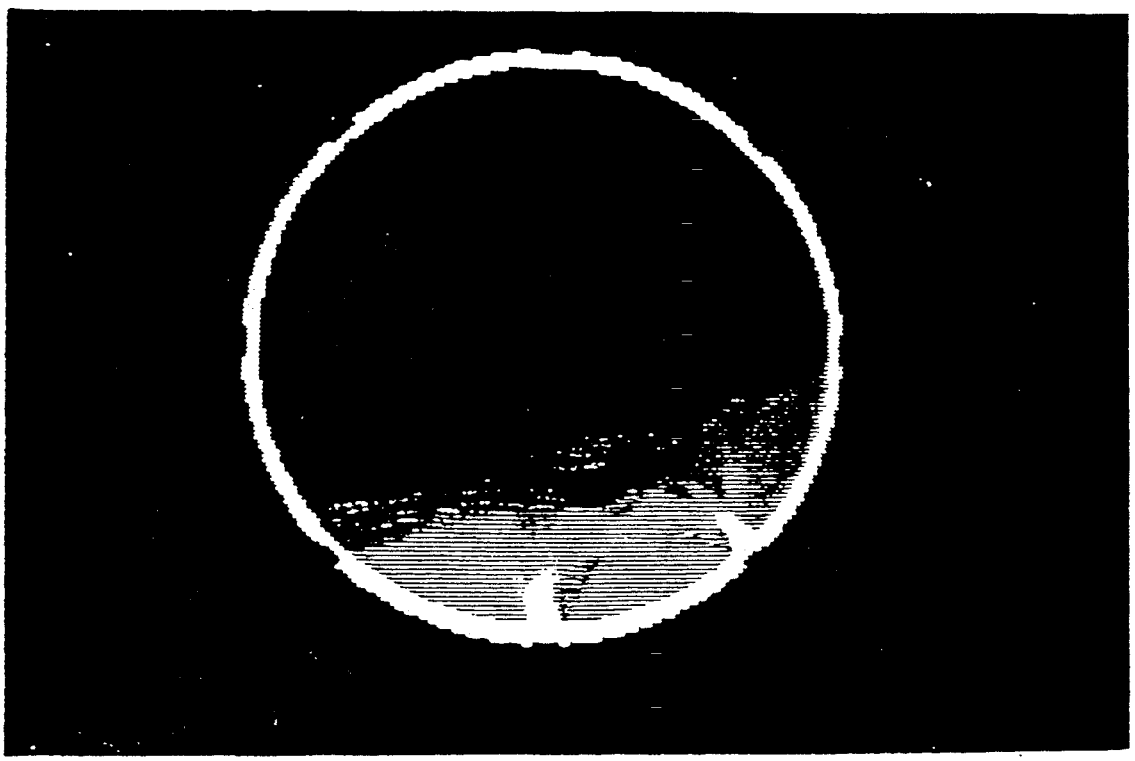
Figure 11B:

FIGS. 3A to 3D indicate positive sensing areas for the electrode pairs producing the sensitivity distributions of FIGS. 2A to 2D respectively;

FIG. 4 illustrates the boundaries of individual image pixels produced by the intercepting positive sensing areas shown in FIG. 3;

FIG. 5 illustrates the circuit formed by one pair of sensor electrodes and one charge measuring circuit associated with one of those electrodes;

FIG. 6 illustrates a clock and four switch control waveforms which appear in the circuit of FIG. 5;

FIG. 7 is a cross-section parallel to the axis of the electrode assembly schematically illustrated in FIG. 1;

FIG. 8 is a cross-section on the line 8—8 of FIG. 7;

FIG. 9 is a schematic circuit diagram of the electrode assembly of FIG. 1 and the various charge measuring circuits associated with the electrodes of that assembly;

FIG. 10 illustrates the effect of overlapping positive and negative sensing areas; and FIGS. 11A and 11B illustrate images produced by the previously described embodiment of the invention from a pipe which is partially filled with static sand, the remaining area being occupied by air.

Referring to FIG. 1, the illustrated system provides a non-invasive and low cost flow imaging system which relies upon electrodes mounted on the outer surface of a fluid conveying pipe and an image reconstruction algorithm of linear back-projection to produce a cross-sectional image of a two-component flow. Such a system could be used for example to detect water separation in horizontal oil and water two-component flow pipelines and for detection of the flow regime and quantitative measurement of component flow rates in oil and gas mixtures.

As shown in FIG. 1, an electrically insulating pipe 10 has flowing through it a fluid made up of two different components 11 and 12. The two components could, for example, be oil and water. Positioned around the outside of the electrically insulating pipe 10 is an array of eight electrodes which are numbered 1 to 8. Each of these electrodes is connected to a CMOS switching array 13 which is controlled by a multiplexing control circuit 14 to connect the inputs received from the electrodes 1 to 8 to a capacitance to voltage transducer array 15. This provides analogue outputs to a multiplexer 16 the output of which is applied to an analogue to digital converter 17. The converter 17 supplies digital data to an image reconstruction computer 18 and is in turn controlled by conversion control signals supplied from the computer 18. The computer 18 also provides control signals to the multiplexing control circuit 14. Thus, the entire system is in effect controlled by the computer 18.

The transducer array 15 converts discharge currents received from the electrodes 1 to 8 into voltages proportional in magnitude to the sensor capacitances of the array of capacitors defined by the various pairs of electrodes surrounding the pipe 10. The multiplexing control circuit 14 is operative to control the CMOS switch array 13 such that all possible combinations of electrode pairs are selected and their capacitance measured in a predetermined order.

In a complete cycle of operation, the capacitances of each of the electrode pairs 1-2, 1-3, 1-8, 2-3, ... 2-8, .. . 7-8 are measured, producing a total number of 28 independent measurements. Each of these measurements in effect interrogate at different area of the pipe, producing a measured capacitance value which is primarily a function of the component concentration and distribution in the measured area. From the measured capacitance data, an image is reconstructed using an algorithm based on the same general principle of back-projection used in conventional medical imaging, the system being modified such that the measured data is back-projected onto positive sensing areas of the 28 capacitance sensor pairs.

FIG. 2 shows the sensitivity distribution of electrode pairs 1-2, 1-3, 1-4 and 1-5 where the sensor capacitance increment caused by a unit dielectric increment (normalised by the standing sensor capacitance and multiplied by a factor of one thousand) is mapped over the pipe cross-section. In each of these distributions there is an area between the electrode pair where the sensitivity is positive, whereas in other areas in the pipe the measurement is insensitive or responds negatively to a dielectric increment. Distributions for other pairs of electrodes can be obtained by rotating the four typical patterns shown in FIGS. 2A to 2D around the pipe's centre.

FIGS. 3A to 3D illustrate representations of the positive sensing areas indicated by the distributions of FIGS. 2A to 2D respectively. To simplify the image reconstruction process, it can be assumed that any change in a measured capacitance results from a homogenous change in the permativity over the entire positive sensing area of each electrode pair. In reconstructing the image, this positive sensing area is given a uniform grey level whose value depends on the measured capacitance value. By summing the 28 resultant grey areas an appropriate cross-sectional image of the flow can be obtained and improved as desired by appropriate filtering.

The reconstruction algorithm is implemented by firstly determining the positive sensing areas of all 28 pairs of electrodes using finite element analysis methods. This produces the results illustrated in FIGS. 3A to 3D. Thereafter, the boundaries of all 28 positive areas are plotted on the pipe cross-section. These boundaries intercept each other, forming many small pixels as illustrated in FIG. 4. Each of the pixels comprises an area which overlaps the unique selection of one or more of the total 28 positive areas. Therefore, each pixel can be related to a 28-element vector with each element corresponding to one of the 28 positive sensitivity areas. Each element in the vector has the value 1 if the pixel is within the corresponding area and 0 if it is not within the corresponding area. The appropriate grey level for each pixel can be obtained by multiplying the pixel vector with the vector consisting of the 28 measurement values obtained from the electrode array. The image pixels can then be processed by appropriate filtering to eliminate artifacts produced by the back-projection before the image is displayed.

It will be appreciated that for the above-described system to work effectively it is necessary to measure very small changes in capacitance accurately. For the eight electrode system illustrated in FIG. 1, most of the standing sensor capacitances are somewhat less than 1pF, whereas the required measurement resolution is typically less than 0.005pF. The presence of stray capacitances accordingly causes difficulties in achieving highly sensitive and stable capacitance measurements.

FIG. 5 illustrates a circuit suitable for use in monitoring the capacitance defined between any pair of electrodes in the eight electrode array of FIG. 1. In FIG. 5, the points identified by numerals 1 and 2 correspond to electrodes 1 and 2 of FIG. 1, the capacitor 19 corresponds to the capacitance defined between electrodes 1 and 2, the capacitor 20 corresponds to the stray capacitance between electrode 1 and the surrounding components other than electrode 2, and capacitor 21 corresponds to the stray capacitance between the electrode 2 and the components surrounding it other than the electrode 1. Four CMOS switches 24 are synchronised by a digital clock signal which is the uppermost waveform of FIG. 6. The switches 22 to 25 are turned on and off by the waveforms identified by the switch numbers in FIG. 6. Thus, in the first half of a typical measurement cycle, switches 23 and 24 are closed to charge the sensor capacitance represented by capacitor 19 to the supply voltage Vc. The charge stored is equal to the product of the sensor capacitance and the supply voltage.

In the second half of the measurement cycle, switches 23 and 24 open and switches 22 and 25 close, thereby discharging the sensor capacitance to earth potential through a charge measuring circuit 26. The charge measuring circuit has an input capacitor 27, for example of 0.1μF, a filtering capacitor 28 (typically 1200 to 4700 pF) and a gain setting resistor 29. An output voltage $V_o$ is developed at terminal 30 which is representative of the sensor capacitance.

The stray capacitance at electrode 1 represented by capacitor 20 is discharged to earth through switch 22 and thus has no affect on the measurement. The stray capacitance at electrode 2 represented by capacitor 21 is held at either earth or virtual earth (the input of the operational amplifier of the charged measuring circuit) potential throughout the measurement process. Thus, this stray capacitance also has virtually no effect on the measurement. The elimination of these stray capacitances enables the transducer to achieve a very low base line drift of for example 0.002 pF in twelve hours, thus ensuring the accuracy of the capacitance measurement. It will be appreciated that circuitry must be provided to enable an equivalent circuit to perform the functions referred to with reference to FIG. 5 in respect of each of the 28 pairs of electrodes which are scanned in a single measurement cycle. Further details of these circuits are described below with reference to FIG. 9.

Referring to FIGS. 7 and 8, the structure of the eight electrode array of FIG. 1 and an associated guard are illustrated in detail. FIG. 7 is a section taken on line 7—7 of FIG. 8. A guard 31 forms a cylindrical casing around the electrode array and extends axially beyond the ends of each electrode by a distance approximately equal to the length of each electrode, the guard 31 being spaced from the electrodes 1 to 8 by an insulating material. The length of each electrode corresponds approximately to the diameter of the pipe 10 through which the flow to be monitored passes. The radial distance between the electrodes and the adjacent portion of the guard 31 is not critical providing radial projections 32 extend radially inwards from that portion of the guard 31 to contact the exterior or the pipe 10. Thus, each radial projection 32 extends between adjacent edges of adjacent electrodes. This reduces the standing capacitances of the adjacent electrodes considerably and thereby enables a higher sensitivity to be selected for the capacitance measuring circuitry.

In order to enhance the quality of the reconstructed images produced on the basis of the measured capacitances, the sensitivity of each measurement should be focussed into a relatively narrow area between the selected electrode pair. Well focussed areas of positive sensitivity result in a larger number of smaller image pixels as can be appreciated from FIG. 4. Such sensitivity focussing can be achieved by effectively using all but the pair of electrodes selected for measurement purposes as a guard ring for the selected pair. In addition, to enhance the data collection speed, a parallel measurement mode can be used in which the capacitances between several pairs of selected electrodes are measured simultaneously. This process can best be explained by reference to FIG. 9.

FIG. 9 shows electrodes 1 to 8 as in the case of FIG. 1. In a complete data collection cycle, each of the electrodes 1 to 7 is connected to a supply voltage $V_c$ in turn. Each of the seven other electrodes which at any one time is not connected to the supply $V_c$ is either connected directly to earth or to the input of a charge detection circuit. Since the input of each charge detection circuit is at virtual earth seven out of the eight electrodes are always held at earth potential and thus in measuring the charge flowing through one of these electrodes, the other six function as a guard ring to it.

At the start of a data collection cycle, electrode 1 is first selected as the active electrode and is charged and discharged at the clock frequency (see FIG. 5 and FIG. 6). During this time the electrodes 2 to 8 are used as detecting electrodes and the capacitance developed between the electrode 1 and electrodes 2 to 8 are measured simultaneously in separate charge detection circuits. Next, the electrode 2 is selected as the active electrode, electrodes 3 to 8 being detecting electrodes. In this part of the cycle electrode 1 is simply earthed. This process continues until finally electrode 7 is active, electrode 8 is the sole detecting electrode, and electrodes 1 to 6 are all earthed.

The above arrangement ensures all electrodes except the active electrode are held at earth or virtual earth potential and the stray-immune capacitance measuring circuit operates in accordance with the explanation of FIG. 5 given above to enable measurements to be formed simultaneously without one measurement influencing the other. The detecting electrodes act as guard rings to each other. Thus, for example, when measuring the capacitance between electrode pair 1 and 5, all the other electrodes are at the same potential as electrode 5.

The above-described arrangement results in the sensitivity distribution patterns shown in FIG. 2, where the sensitivity of each measurement is confined to a narrow area between the selected electrodes and the measurement is insensitive or responds negatively to dielectric changes outside this area. Such negative sensitivities have beneficial effects on the image reconstruction. In reconstructing the image, each of the 28 positive sensing areas is given a grey level whose value depends on the single related measured capacitance value. It will be noted that if an object is present outside the positive sensing area of an electrode pair the measurement made with this pair produces a negative value, and hence a negative grey level in this area. By superimposing all the 28 positive sensing areas over the pipe cross-section, the grey level in the area where the object is present will be enhanced, whereas in other areas the grey level will be reduced due to the negative grey levels mentioned above. This reduces the inherent artifacts generated by the back-projection process.

The effect of the negative sensitivity is illustrated by FIG. 10, where an object 98 is located adjacent that portion of the wall of the pipe supporting electrode 2. The positive sensing area of the electrode pair 2-6 is indicated by area 99 whereas the positive sensing area of electrode pair 5-7 is indicated by area 100. The effect of the object 98 close to electrode 2 will result in a uniform grey level across the area 99. The remoteness of the object 98 from the area 100 however will be such that the object will produce a negative grey level for the area 100. The superimposition of these two grey levels will tend to reduce the grey level in the overlapping area of the two areas 99 and 100.

Similarly, other positive sensing areas which do not contain the object 98 will have negative grey levels and these negative grey levels reduce the artifacts in these areas. By summing the grey levels of all the electrode pair combinations, an image can be generated which is an approximation to the true distribution of the localised object 98 within the pipe 10.

Because of the particular geometrical arrangement of the sensor electrodes, measurements made with different electrode pairs have very different sensitivities, the sensitivity being the ratio of sensor capacitance change to a unit increment in permittivity of the sensing area. Thus, for the electrode pairs 1-2, 1-3, 1-4 and 1-5 sensitivity ratios of 16, 1.9, 1.2 and 1 respectively are found. Because of these wide differences in sensitivity it is difficult to design a single capacitance measuring circuit which is suitable for such a large input dynamic range. For example, the gain of a particular capacitance measuring circuit must not be too high, in order to avoid saturation when adjacent electrodes are selected, but must be sufficiently high, in order to detect dielectric changes in the central area of the pipe lying between relatively remote electrode pairs. Capacitance sensors of the type illustrated in FIG. 1 have an inherent low sensitivity in a central area of the pipe.

This problem can be overcome by using an array of detectors having different gains. This is illustrated in detail in FIG. 9 which shows a series of switches 33 to 75 controlling the connector of the electrodes 1 to 8 to various potential sources and a series of charge detector circuits 76 to 97. Charge detectors 76, 78, 81, 82, 86, 90 and 94 have a sensitivity appropriate to measurements made between immediately adjacent electrodes, for example electrodes 1 and 2. Detectors 77, 80, 83, 87, 91 and 95 have sensitivities appropriate for measurements made between pairs of electrodes separated by a single electrode, for example electrodes 1 and 3. Detectors 79, 84, 88, 92 and 96 have sensitivities appropriate for measurements made between electrodes separated by two electrodes, for example electrodes 1 and 4. Detectors 85, 89, 93 and 97 have sensitivities appropriate for measurements made between electrodes separated by three other electrodes, for example electrodes 1 and 5. Thus, when a measurement cycle is initiated, electrode 1 is chosen to be charged and discharged by switches 34 and 33. Switches 37, 41, 46, 53, 59, 65 and 71 are selected enabling charge detectors 76, 77, 79, 85, 88, 91 and 94 to operate. In the next portion of the cycle, electrode 2 is chosen to be charged and discharged by switches 35 and 36, and electrode 1 earthed by switch 33. Switches 43, 48, 54, 60, 66 and 72 are selected enabling detectors 78, 80, 84, 89, 92 and 95 to operate. The cycle continues with the appropriate switches being selected to set the appropriate charge detector sensitivity.

Although a reconstruction algorithm can be derived by adaptation of the general principle of the back-projection methods used in medical imaging, the particular approach adopted is especially suitable for systems based upon capacitance sensing. The techniques used in medical conductance imaging systems are in many ways analogous to those used in capacitance systems. The reconstruction algorithm of such medical imaging systems approximate to electrical equal potentials using arcs of circles and measured data is back-projected onto the areas defined by these boundaries. In the method employed in the system described above the measured capacitance value is back-projected onto the positive sensing area of each electrode pair. However, the boundaries of the sensing pairs are calculated for the actual sensor structure shown in FIGS. 7 and 8 using finate element analysis methods and hence the image pixels obtained are more accurate in shape and position.

In calculating the measurement sensitivity distributions of the electrodes it has been assumed that there is a homogenous permittivity over the entire cross-section of the pipe. However, the component distribution of the flows is usually not homogeneous. The in-homogeneity of the distribution causes distortion of the electric field between the electrodes, and hence affects the shape of the sensitive areas from the idealised shape as illustrated in FIG. 2 or 3. This results in distortion of the reconstructed image.

This problem becomes serious where a flow comprises large concentrations of water as water has a large permittivity and a relatively high conductivity. To overcome these problems an iterative approach can be used. This involves recalculating the sensitivity areas using the distorted image generated from the first back-projection, reproducing the image using the newly calculated sensitive areas, and then recalculating the sensitive areas again using the new image. This process can be repeated until an undistorted image is approached.

The image processing techniques described above include pixel grey level weighting and threshold filtering. The pixel weighting may be based on an expert's knowledge of typical distribution patterns of two component flows and the sensitivity distribution of the electrodes as illustrated in FIG. 2. For instance, the sensitivity in the central area of the pipe is relatively small and therefore in image processing the grey level of the pixels around the pipe centre is preferably weighted by a factor dependent upon the measurement data.

FIGS. 11A and 11B illustrate images obtained as described above of a stratified sand/air flow measured in a horizontal pipe when the sand is stationary. The illustrations indicate the results obtained directly from the back-projection. Thus, the images are clearly comprehensible even before filtering.

In multi-component flows, the components often travel at several meters per second. Therefore the speed of the imaging system data collection is very important. In the described arrangement, the data collection process can be relatively fast, for example five milliseconds for 28 measurements, this being enough for most applications. The image reconstruction speed can be made sufficiently fast by using parallel array processors for the reconstruction computer.

We claim:

1. A tomographic flow imaging system, comprising three or more capacitance electrodes monitored passes, means for measuring the capacitance between each pair of the electrodes, and means for deriving from the measured capacitances an output representative of the distribution of material within the pipe, wherein means are provided for applying a predetermined voltage signal to one electrode at a time, and means are provided for connecting each electrode other than said one electrode to sources of equal fixed potential, the capacitance of each pair of electrodes being measured by measuring charge flowing between the said other electrode of the pair and the source of potential to which it is connected.

2. A tomographic flow imaging system according to claim 1, wherein the assembly of electrodes is housed within a conductive guard which extends around the pipe and is connected to one of said sources of equal fixed potential.

3. A tomographic flow imaging system according to claim 2, wherein the guard comprises ribs which project radially inwards between adjacent electrodes.

4. A tomographic flow imaging system according to claim 1, comprising switching circuits for connecting each of the electrodes either to the predetermined voltage signal or alternatively to a respective charge measuring circuit the input of which is at the said equal fixed potential.

5. A tomographic flow imaging system according to claim 4, wherein switching circuits are arranged such that all the measuring circuits operate simultaneously.

6. A tomographic flow imaging system according to claim 4 or 5, wherein each charge measuring circuit comprises an array of measuring circuits of different sensitivities, the respective switching circuit selecting a measuring circuit from the array which has a sensitivity appropriate to the electrode pair the capacitance between which is to be measured.

7. A tomographic flow imaging system according to claim 4 or 5 wherein the switching circuits are arranged such that for each pair of electrodes between which the capacitance is to be measured there are four switches, a first pair of the four switches being arranged to close simultaneously such that one electrode is connected to the said voltage signal and the other electrode is connected to a said source of fixed potential, and the other pair of the four switches being arranged to close after opening of the first pair such that the said one electrode is connected to a said source of fixed potential and the other electrode is connected to a charge measuring circuit.

8. A tomographic flow imaging system according to claim 1, wherein the means for deriving an output representative of the distribution of material within the pipe comprises means for constructing an image representative of the distribution, the image constructing means being operative to back-project the measured capacitance values onto positive sensing areas of the fields developed between the pairs of electrodes between which the capacitance values are measured.

9. A tomographic flow imaging system according to claim 8, comprising means for defining a series of positive elements each made up from a different combination of parts of the various positive sensing areas, and means for calculating the grey level of each element by summing the contributions of each positive sensing area within which that element is included.

10. A circuit for measuring the capacitance of a capacitor formed by a pair of electrodes, comprising first and second pairs of switches arranged such that one switch of each pair is connected to a respective electrode, wherein a first switch of the first pair is connected between its respective electrode and a first source of fixed potential, a second switch of the first pair is connected between its respective electrode and a second source of fixed potential, a first switch of the second pair is connected between its respective electrode and the second source of fixed potential, and the second switch of the second pair is connected between its respective electrode and an input to a charge measuring circuit, the said input being maintained at the potential of the said second source of fixed potential, and means being provided to close the first pair of switches to charge the said capacitor, and to then open the first pair of switches and close the second pair of switches to discharge the capacitor into the charge measuring circuit.

* * * * *